(12) United States Patent
Sköld et al.

(10) Patent No.: US 10,406,088 B2
(45) Date of Patent: Sep. 10, 2019

(54) VERSATILE TOPICAL DRUG DELIVERY VEHICLE AND MULTIFACTORIAL TISSUE MOISTURIZER THAT PROVIDES MUCOSAL AND SKIN BARRIER RESTORATION

(71) Applicant: TetraDerm Group LLC, New York, NY (US)

(72) Inventors: Thomas Sköld, Norrtälje (SE); Georgia Levis, New York, NY (US); Michael J. Burns, Grosse Point Farms, MI (US)

(73) Assignee: TetraDerm Group LLC, New York, NY (US)

( * ) Notice: Subject to any disclaimer, the term of this patent is extended or adjusted under 35 U.S.C. 154(b) by 0 days.

(21) Appl. No.: 14/978,108

(22) Filed: Dec. 22, 2015

(65) Prior Publication Data
US 2016/0206538 A1    Jul. 21, 2016

Related U.S. Application Data

(60) Provisional application No. 62/105,325, filed on Jan. 20, 2015.

(51) Int. Cl.
| | | |
|---|---|---|
| *A61K 8/46* | (2006.01) | |
| *A61K 8/14* | (2006.01) | |
| *A61K 8/42* | (2006.01) | |
| *A61Q 19/00* | (2006.01) | |
| *A61K 8/44* | (2006.01) | |
| *A61K 8/63* | (2006.01) | |
| *A61K 8/49* | (2006.01) | |
| *A61K 8/36* | (2006.01) | |
| *A61K 8/365* | (2006.01) | |
| *A61K 8/67* | (2006.01) | |

(52) U.S. Cl.
CPC ........... *A61K 8/466* (2013.01); *A61K 8/14* (2013.01); *A61K 8/361* (2013.01); *A61K 8/365* (2013.01); *A61K 8/42* (2013.01); *A61K 8/44* (2013.01); *A61K 8/4913* (2013.01); *A61K 8/4946* (2013.01); *A61K 8/63* (2013.01); *A61K 8/671* (2013.01); *A61Q 19/00* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 4,326,055 A | 4/1982 | Loeliger | |
| 4,508,703 A | 4/1985 | Redziniak | |
| 4,610,868 A | 9/1986 | Fountain et al. | |
| 4,739,098 A | 4/1988 | Chandraratna | |
| 5,196,190 A | 3/1993 | Nangia et al. | |
| 5,206,020 A | 4/1993 | Critchley et al. | |
| 5,298,246 A | 3/1994 | Yano et al. | |
| 5,320,906 A | 6/1994 | Eley et al. | |
| 5,391,373 A | 2/1995 | Mausner | |
| 5,468,475 A | 11/1995 | Shaku et al. | |
| 5,534,499 A | 7/1996 | Ansell | |
| 5,565,213 A * | 10/1996 | Nakamori | A61K 9/127 424/450 |
| 5,593,622 A | 1/1997 | Yoshioka et al. | |
| 5,628,936 A | 5/1997 | Wallach | |
| 5,631,012 A | 5/1997 | Shanni | |
| 5,643,899 A | 7/1997 | Elias et al. | |
| 5,665,379 A | 9/1997 | Hersloef et al. | |
| 5,733,572 A | 3/1998 | Unger et al. | |
| 5,776,480 A | 7/1998 | Candau et al. | |
| 5,817,856 A | 10/1998 | Tirosh et al. | |
| 5,820,873 A | 10/1998 | Choi et al. | |
| 5,853,755 A * | 12/1998 | Foldvari | A61K 9/0014 264/4.1 |

(Continued)

FOREIGN PATENT DOCUMENTS

| | | |
|---|---|---|
| CA | 2281430 A1 | 12/2000 |
| EP | 0087993 A1 | 9/1983 |

(Continued)

OTHER PUBLICATIONS

WO2006018149A1 translation, "Cosmetic compositions for treating stressed skin containing taurine and long-chained fatty alcohols" accessed from:https://www.google.ch/patents/WO2006018149A1?cl=en&dq=TEWL+taurine&hl=de&sa=X&ved=0ahUKEwiP2cKm6cDSAhUD4CYKHbUlAjUQ6AEIITAB, accessed on Mar. 6, 2017, pp. 1-16.*
Bellemere, G., et al., "Retinoic Acid Increases Aquaporin 3 Expression in Normal Human Skin", Soc. Inv. Derm., 2007, pp. 542-548.*
Loo, CH., et al., "Effect of compositions in nanostructured lipid carriers (NLC) on skin hydration and occlusion", Int. J. Nanomed., 2013, pp. 13-22.*
Raney, S.G., "The effect of bilayer and hexagon HII phase lipid films on transepidermal water loss", Ex. Derm. 2006, pp. 493 (Year: 2006).*

(Continued)

*Primary Examiner* — Michael G. Hartley
*Assistant Examiner* — Lance W Rider
(74) *Attorney, Agent, or Firm* — Moser Taboada

(57) ABSTRACT

Provided is a topical formulation comprising (1) three or more of the following four components a through d, or (2) component c and one or more of components a, b or d: (a) a skin barrier repair formulation comprising fatty acid, bilayer-stabilizing steroid, and complex lipid (CL), wherein the weight ratio of CL to steroid is from about 1.5:1 to about 8:1, and the weight ration of CL to FA is from about 4:1 to about 1:1, the lipids present in an amount from about 3% wt. to about 10% wt.; (b) a natural moisturizer formulation, wherein the natural moisturizers are urea, urocanic acid, pyrrolidone-5-carboxylic acid, lactic acid or free amino acid; (c) one or more retinoids in an amount from about 0.01% wt. to about 10% wt.; or (d) taurine in an amount from about 0.1% wt. to about 5% wt.

14 Claims, 4 Drawing Sheets

(56) References Cited

U.S. PATENT DOCUMENTS

| | | | |
|---|---|---|---|
| 5,869,068 A * | 2/1999 | De Lacharriere | A61K 8/44 424/401 |
| 5,942,245 A | 8/1999 | Katinger et al. | |
| 5,993,830 A | 11/1999 | Freij | |
| 6,132,763 A | 10/2000 | Fisher | |
| 6,153,209 A | 11/2000 | Vega et al. | |
| 6,214,375 B1 * | 4/2001 | Modi | A61K 9/1271 424/1.11 |
| 6,238,694 B1 | 5/2001 | Gasco | |
| 6,419,949 B1 | 7/2002 | Gasco | |
| 6,497,888 B1 | 12/2002 | Morancais et al. | |
| 6,521,237 B2 * | 2/2003 | Cole | A61K 8/365 424/400 |
| 6,586,000 B2 | 7/2003 | Luo et al. | |
| 6,730,288 B1 | 5/2004 | Abram | |
| 6,824,785 B1 | 11/2004 | Kitson et al. | |
| 6,932,963 B2 | 8/2005 | Perricone | |
| 6,936,272 B2 | 8/2005 | Martin et al. | |
| 2002/0048596 A1 | 4/2002 | Cevc | |
| 2002/0064524 A1 | 5/2002 | Cevc | |
| 2003/0099694 A1 | 5/2003 | Cevc et al. | |
| 2004/0009213 A1 | 1/2004 | Skold | |
| 2004/0071767 A1 | 4/2004 | Cevc et al. | |
| 2005/0123897 A1 | 6/2005 | Cevc et al. | |
| 2005/0129722 A1 | 6/2005 | Skold | |
| 2006/0121583 A1 | 6/2006 | Lassalle et al. | |
| 2007/0009474 A1 * | 1/2007 | Xie | A61K 8/345 424/74 |
| 2007/0031483 A1 | 2/2007 | Cevc | |
| 2007/0042030 A1 | 2/2007 | Cevc | |
| 2007/0184114 A1 | 8/2007 | Cevc | |
| 2009/0081139 A1 | 3/2009 | Skold | |
| 2010/0166814 A1 * | 7/2010 | Dumas | A61K 8/14 424/401 |
| 2010/0184733 A1 | 7/2010 | Korevaar et al. | |
| 2010/0247454 A1 * | 9/2010 | Mitts | A61K 31/685 424/49 |
| 2010/0286102 A1 | 11/2010 | Vielhaber | |
| 2011/0177140 A1 | 7/2011 | Voegeli et al. | |
| 2013/0017239 A1 | 1/2013 | Viladot Petit et al. | |
| 2013/0280308 A1 | 10/2013 | Roy et al. | |
| 2015/0024077 A1 | 1/2015 | Batchvarova et al. | |

FOREIGN PATENT DOCUMENTS

| | | |
|---|---|---|
| EP | 0176034 A2 | 4/1986 |
| EP | 0711558 A1 | 5/1996 |
| EP | 1092428 A1 | 4/2001 |
| FR | 2794366 A1 | 12/2000 |
| GB | 2379386 A | 12/2001 |
| JP | 2001004874 A | 1/2001 |
| JP | 2001048721 A | 2/2001 |
| JP | 5023323 B2 * | 9/2012 |
| KR | 101338237 B1 | 12/2013 |
| NZ | 254392 A | 7/1997 |
| WO | WO-9325530 A2 | 12/1993 |
| WO | WO-9417796 A1 | 8/1994 |
| WO | WO-9620914 A1 | 7/1996 |
| WO | WO-9629069 A1 | 9/1996 |
| WO | WO-9637192 A1 | 11/1996 |
| WO | WO-9712598 A2 | 4/1997 |
| WO | WO-9817253 A1 | 4/1998 |
| WO | WO2006018149 A1 * | 2/2006 |
| WO | WO-2008/079898 | 7/2008 |

OTHER PUBLICATIONS

Loden 1, "Dry skin and Moisturizers", CRC Press, 2000, pp. 340 (Year: 2000).*

Loden 2, "Urea-containing moisturizers influence barrier properties of normal skin", Arch Derm. Res., 1996, pp. 103-107 (Year: 1996).*

Lee, Y., et al., "Changes in Transepidermal Water Loss and Skin Hydration according to Expression of Aquaporin-3 in Psoriasis", Ann Derm. 2012, pp. 168-174 (Year: 2012).*

Murota, H., et al., "Topical cholesterol treatment ameliorates hapten-evoked cutaneoushypersensitivity by sustaining expressi on of 11b-HSD1 in epidermis", Exp. Derm. 2013, pp. 58-77 (Year: 2013).*

Harvard, "Occlusive ingredients in moisturizers", Harvard Health Publishing, printed on Mar. 5, 2018, pp. 1-2 (Year: 2018).*

JP5023323B2 translation, "Expression-enhancing agent of aquaporin 5", printed on Mar. 5, 2018, printed from: https://patents.google.com/patent/JP502332362/en?oq=JP502332362, pp. 1-10 (Year: 2018).*

Visscher, M.O. et al. "Effect of soaking and natural moisturizing factor on stratum corneum water-handling properties", J. Cosmet. Sci., 2003, pp. 289-300 (Year: 2003).*

Silvander et al., "A Method to Detect Leakage of DNA Intercalators through Liposome Membranes." Analytical Biochemistry 242, 40-44 (1996) Article No. 0425, May 6, 1996.

Fletcher et al., "Gene Expression Analysis of EpiDerm Following Exposure to SLS Using cDNA Microarrays", Toxicology in Vitro, vol. 15, Issues 4-5, pp. 393-398, Aug.-Oct. 2001.

Janeke et al., "Role of Taurine Accumulation in Keratinocyte Hydration", Journal of Investigative Dermatology, vol. 121, Issue 2, pp. 354-361, Aug. 2003.

Grafe et al., "Functional Characterization of Sodium- and Chloride-Dependent Taurine Transport in Human Keratinocytes", European Journal of Pharmaceutics and Biopharmaceutics, vol. 57, Issue 2, pp. 337-341, Mar. 2004.

Warskulat et al., "The Osmolyte Strategy of Normal Human Keratinocytes in Maintaining Cell Homeostasis", Journal of Investigative Dermatology, vol. 123, Issue 3, pp. 516-521, Sep. 2004.

Rockel et al., "The Osmolyte Taurine Protects Against Ultraviolet B Radiation-Induced Immunosuppression", J Immunol, vol. 179, Issue 6, pp. 3604-3612, Sep. 15, 2007.

Silva et al., "Penetration Profile of Taurine in the Human Skin and Its Distribution in Skin Layers", Pharmaceutical Research, vol. 25, Issue 8, pp. 1846-1850, Aug. 2008.

Warskulat et al., "Ultraviolet a Induces Transport of Compatible Organic Osmolytes in Human Dermal Fibroblasts", Experimental dermatology, vol. 17, Issue 12, pp. 1031-1036, Dec. 2008.

Angelo, "Vitamin A", Linus Pauling Institute, Oregon State University, 2013.

Chesney et al., "Differential Regulation of TauT by Calcitriol and Retinoic Acid via VDR/RXR in LLC-PK1 and MCF-7 Cells", Taurine 8, Springer New York, pp. 291-305, 2013.

International Search Report and Written Opinion dated Apr. 14, 2016 for PCT Application No. PCT/US2015/067314.

Mao-Qiang, et al., A natural lipid mixture improves barrier function and hydration in human and murine skin, Journal of the Society of Cosmetic Chemists, 1996, vol. 47, pp. 157-166.

International Search Report and Written Opinion dated Mar. 28, 2017 for Application No. PCT/US2016/040946, 12 pages.

European Search Report for Application No. 15879257.2, dated Aug. 20, 2018, 9 pages.

* cited by examiner

VERSATILE TOPICAL DRUG DELIVERY VEHICLE AND MULTIFACTORIAL TISSUE MOISTURIZER THAT PROVIDES MUCOSAL AND SKIN BARRIER RESTORATION

This application claims benefit of U.S. Provisional Patent Application Ser. No. 62/105,325 filed Jan. 20, 2015, which is hereby incorporated in its entirety.

The present application relates generally to topical formulations useful for moisturizing skin or preventing, ameliorating or repairing skin damage.

There is a continuing need in the art for topical formulations that do one or more of improve moisturization of skin or mucosa, improve moisturization of skin or mucosa after damage, improve skin or mucosa recovery after damage, improve TEWL after damage in skin or mucosa (such as without substantial occlusion), improve moisture retention in skin or mucosa (such as without substantial occlusion), or improve moisture retention in skin or mucosa after damage (such as without substantial occlusion).

SUMMARY

Provided in one embodiment is a topical formulation comprising (1) three or more of the following four components a through d, or (2) component c and one or more of components a, b or d: (a) a skin barrier repair formulation comprising lipids that are fatty acid (FA), bilayer-stabilizing steroid (CH), and complex lipid (CL), wherein the skin barrier repair formulation is present in an amount that enhances skin barrier repair, wherein the weight ratio of CL to CH is from about 1.5:1 to about 8:1, and the weight ration of CL to FA is from about 4:1 to about 1:1, the lipids present in an amount from about 3% wt. to about 10% wt.; (b) a natural moisturizer formulation, wherein the natural moisturizers are selected from the group consisting of urea, urocanic acid (UCA), pyrrolidone-5-carboxylic acid (PCA), lactic acid and free amino acid, the natural moisturizer formulation present in a skin moisturizing amount; (c) one or more retinoids in an amount from about 0.01% wt. to about 10% wt.; or (d) taurine in an amount from about 0.1% wt. to about 5% wt. In embodiments, if the formulation comprises components a and c, then it further comprises one or more of b and d.

Provided in one embodiment is a topical formulation comprising (1) three or more of the following four components a through d, or (2) component c and one or more of components a, b or d: (a) a skin barrier repair formulation comprising lipids that are fatty acid (FA), bilayer-stabilizing steroid (CH), and complex lipid (CL), wherein the weight ratio of CL to CH is from about 1.5:1 to about 8:1, and the weight ration of CL to FA is from about 4:1 to about 1:1, the lipids present in an amount from about 3% wt. to about 10% wt.; (b) a natural moisturizer formulation, wherein the natural moisturizers are selected from the group consisting of urea, urocanic acid (UCA), pyrrolidone-5-carboxylic acid (PCA), lactic acid and free amino acid; (c) one or more retinoids in an amount from about 0.01% wt. to about 10% wt.; or (d) taurine in an amount from about 0.1% wt. to about 5% wt.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1:
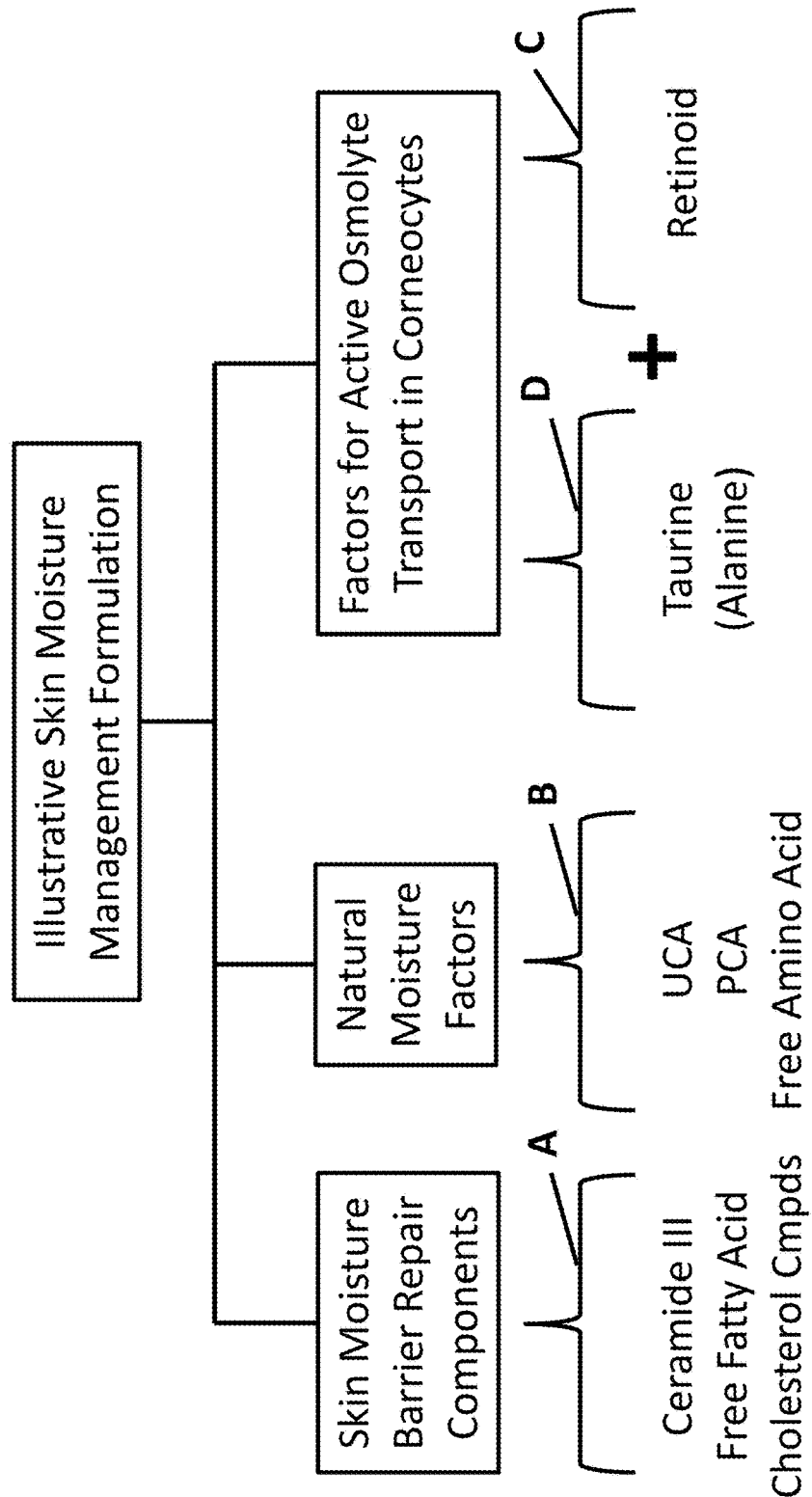
FIG. 1 an illustrative formulation according to the invention.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

An illustrative formulation is shown in FIG. 1. For the purposes of the claims, when component (d) is present the "free amino acids" shall not include taurine.

The compositions of the invention are believed to provide (i) equivalent or better skin (or mucosal) barrier repair and maintenance as measured by recovery and sustained improvement of transmucosal, transepithelial or transepidermal water loss (TEWL) and, in the case of the latter, including after challenge with a sodium dodecyl sulfate (SDS) formulation, as compared to a Comparator Product; and/or (ii) equivalent or better epidermal water retention as measured by epidermal electrical conductance as compared to a Comparator Product. The Comparator Product can be a vehicle form of test product and/or a recognized effective moisturizer base cream found the market in the United States. The Comparator Product can be, for example, Cetaphil (Galderma Laboratories, L.P., Dallas, Tex.). Comparisons for a given product of the invention will typically be against Comparator Product of comparable viscosity. E.g., a lotion will typically be compared to a lotion, a cream to a cream.

In certain embodiments, the topical formulations of the invention facilitate uptake by the skin or mucosa, or the circulatory system (i.e., systemically) of bioactive agents (defined below).

Figure 2:
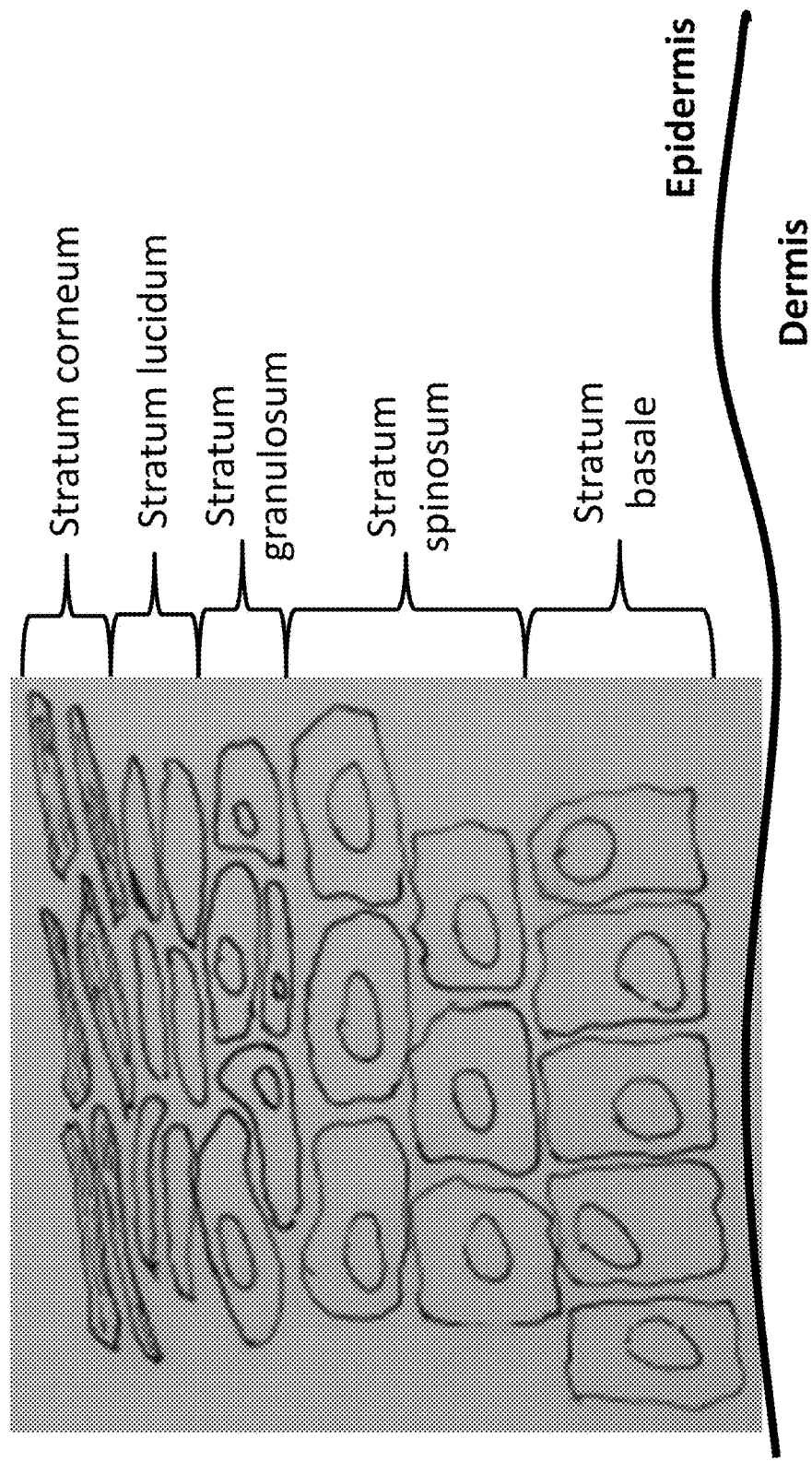
FIG. 2 is an illustration of the structure of the epidermis.

The skin of the human body is comprised of the outer epidermis, and the dermis. The epidermis includes the stratum corneum (outer), stratum lucidum, stratum granulosum, stratum spinosum and stratum basale. See FIG. 2. Epidermal cells migrate outward from the inner stratum basale to outer stratum corneum as they mature and differentiate into to the cell types of the given layers.

During this migration of the epidermal cells to the stratum corneum a high molecular weight histidine-rich structural protein ("profilaggrin") transitions to a lower molecular weight "filaggrin" form. During progression through to the stratum corneum, filaggrin is decomposed to amino acids, some of which are further enzymatically converted, providing much of the skin's "natural moisturizing factor." Filaggrin derived natural moisturizers include free unaltered amino acids, urocanic acid (UCA)(derived from histidine) and pyrrolidone-5-carboxylic acid (PCA)(derived from glutamine) along with, among other things, lactates and urea. These substances are soluble in the fluids that are located both inside the skin cells and the surrounding extracellular milieu. These substances are strong humectants that help retain moisture in the stratum corneum and some are particularly vital to maintaining cellular water balance.

For the most part, the movement of these humectants in and out of the cells of the stratum corneum is by passive osmosis. However, for certain of these osmolytes, there are specific cellular transporter systems that actively transport osmolytes in and out of the cells. These particular osmolytes are vital cytoprotectants (osmoprotectants) that play a key role in maintaining cell volume and fluid balance. For example, when a cell becomes dehydrated and contracts, these transporters, in particular the taurine transporter (TauT), cause membrane channels to be opened and induce the influx of specific osmolytes that carry water with them into the cell, thereby restoring hydration and normal cell volume. Naturally occurring osmoprotectant osmolytes include myoinositol, glycine, alanine and taurine of which the latter is the most abundant.

In embodiments, the amount of natural moisturizers is from about 0.1% wt. to about 10% wt. of the formulation. Weight amounts are calculated assuming no counter-ions, and where possible no net charge. If a counter-ion containing form is used in formulation, the percent amount of the compound is calculated without the counterion.

The names used for the chemicals recited here are intended to include their recognized functional analogs, and the acid or base addition salts of such chemicals and analogs. Forms that readily convert to a functional form in the stratum corneum, such as esters and certain amides, are also included, along with their acid or base addition salts. Such analogs can include chloramine and bromamine derivatives. Typically, acid or base addition salts are pharmaceutically acceptable acid or base addition salts.

Taurine is an important osmotic regulator ("Osmolyte") for epidermal keratinocytes. To maintain cell volume homeostasis taurine is concentrated in the cells of the epidermis via active transport. The taurine transporter (TauT) regulates taurine content, and hence, the hydration of epidermal cells.

In embodiments, the amount of taurine is from about 0.1% wt. to about 5% wt. of the formulation.

While vitamin-A and related retinoids are generally considered necessary to support tissue healing processes, when topically applied these entities are well known to disrupt the skin barrier and to cause dryness, irritation and flaking (Report of the Linus Pauling Institute at Oregon St. Univ. avail. at Ipioregonstate.edu/infocenter/skin/vitamin ("LPI Report")). Nonetheless, if such retinoids are administered to the skin in conjunction with the correct physiological ratio of intercellular lipids and/or their precursors (ceramides, cholesterol esters and fatty acids) and natural moisturizing factor constituents (such as described herein) and appropriate osmolytes (such as taurine and alanine), it is believed that they contribute positively to restoration and maintenance of epidermal cellular hydration by virtue of their ability to induce the up-regulation of critical osmolyte transporters, in particular TauT (e.g., Chesney et al., Adv. Exp. Med. Biol. 2013, 776:291-305).

Retinoic acid and retinoids in general are associated with skin dryness, and thus contraindicated for maintaining hydrated skin. As stated at LPI Report, "[a] very common side effect of topical retinoid therapy is "retinoid dermatitis," also referred to as retinoid irritation or retinoid reaction. Retinoid dermatitis is characterized by erythema, scaling, dryness, and pruritus. Topical retinoids induce changes in the epidermis that lead to increased proliferation and altered differentiation of keratinocytes (see Photoaging); this in turn disrupts the barrier of the skin and contributes to the features of retinoid dermatitis." It is therefore counterintuitive to incorporate retinoic acid or a derivative in a product intended to moisturize the skin. Nonetheless, when presented with component a, component b, or with component c, it serves to cause activation of the TauT with the consequence that the osmoprotectant taurine is actively transported, along with water, into the keratinocyte thus increasing keratinocyte hydration.

Vitamin-A related retinoids include without limitation, retinoic acids (such as, all-trans retinoic acid or 13-cis retinoic acid), retinols (such as all-trans retinol (Tretinoin), 13-cis retinol or 9-cis retinol), comparable retinals (retinaldehydes), hydroxypinacolone retinoate (HPR)(binds directly to retinoic acid receptors), Fenretinide, the retinoids recited in WO1996-029069 (as described therein and in U.S. Pat. Nos. 4,739,098 and 4,326,055; European Patent Application 176034 A, published Apr. 2, 1986 and PCT Patent Applications WO 93/25530 and WO 94/17796, all of which are incorporated herein by reference on their teachings of retinoids), tricyclic retinoids (such as described in WO1996020914, incorporated herein by reference on its teachings of retinoids), adapalene (6-[3-(1-adamantyl)-4-methoxy-phenyl]naphthalene-2-carboxylic acid), tazarotene (ethyl 6-[2-(4,4-dimethyl-3,4-dihydro-2H-1-benzothiopyran-6-yl)ethynyl]pyridine-3-carboxylate), or the like.

In embodiments, the amount of retinoid is from about 0.01% wt. to about 3 or 5% wt. of the formulation. In embodiments, the retinoid component comprises one or more retinols in an amount from about 0.1% wt. to about 5% wt. of the formulation. In embodiments, the amount of retinoid varies with the particular retinoid employed. Those of skill will recognize that higher portions of the range may be used for example with retinol palimate, and lower portions used for example with tretinoin (all-trans retinoic acid).

Of the skin barrier repair formulation, "complex lipids" are phospholipids, ceramides, sphingomyelins, glycosphingolipids, and combinations thereof in a form that can be incorporated in lipid bilayers. In embodiments, phospholipids comprise about 90 mole % or more of the complex lipid, or about 95 mole % or more, or about 97 mole % or more, or about 98 mole % or more, or about 99 mole % or more.

Of the skin barrier repair formulation, the phospholipid can be a mixture of different phospholipid types, including minor amounts of lysophospholipids. In certain embodiments, about 5 mole % or more of the phospholipid has a head group with no net charge. For example, the phospholipid can be made up of phosphatidylcholine or phosphatidylethanolamine. In certain embodiments, about 10 mole % or more, or, about 15 mole % or more, or, about 20 mole % or more, or, about 25 mole % or more, or, about 30 mole % or more, or, about 40 mole % or more, about 50 mole % or more, about 60 mole % or more, about 70 mole % or more, about 80 mole % or more, about 90 mole % or more, of the complex lipid has a head group with no net charge. Typically, only a small percentage, such as about 10 mole % or less, of the complex lipid is lysophospholipid. In certain embodiments, about 8 mole % or less, or, about 7 mole % or less, or, about 6 mole % or less, or, about 5 mole % or less, or, about 4 mole % or less, or, about 3 mole % or less, about 2 mole % or less, about 1 mole % or less, about 0.5 mole % or less, is lysophospholipid.

Of the skin barrier repair formulation, the bilayer stabilizing steroid or steroid analog is typically cholesterol, a fatty acyl ester of cholesterol, or an analog thereof, such as ergosterol, cholestanol, 7-dehydrocholesterol, lanosterol, or the like. Any steroid or steroid analog that stabilizes the bilayer of the vesicles can be used, though steroids or analogs with substantial hormone activity are typically avoided unless intended for use as the bioactive agent.

Of the skin barrier repair formulation, the fatty acid can, for example, be of any composition found in a natural source, including hydrolysis of esterified fatty acids. Or, the fatty acid component can be hydrogenated to remove substantially all or a portion of any unsaturation. In certain embodiments, the fatty acid component is selected such that 50 mole % or more is C12 or higher, or C14, or C16 or higher. In certain embodiments, the fatty acid component is selected such that 50 mole % or more is C22 or lower, or C20 or lower, or C18 or lower. In certain embodiments, 75 mole % or more of the fatty acid component is from C12 or C14 or C16 to C22 or C20 or C18. In certain embodiments, 80 mole % or more, 85 mole % or more, 90 mole % or more, 95 mole % or more, 97 mole % or more, 98 mole % or more, or 99 mole % or more, meets one of the size parameters of this paragraph.

In many embodiments, about 60% wt. or more of the lipid components of skin barrier repair formulation are present in the form of the aggregates structures of lipid vesicles (as defined below) or lipid particles, with about 10% wt. or more present in lipid vesicles and about 10% wt. or more present in lipid particles.

As will be understood by those of ordinary skill in the art of dermatological formulation, the formulations of the invention can be presented as, for example, emulsions, liquid suspensions, creams, gels, lotions or foams. Some embodiments of the invention can be in the form of an emulsion. Emulsions contain both a dispersed and a continuous phase, with the boundary between the phases called the "interface". An emulsion is a mixture of two or more liquids that are normally immiscible (nonmixable or unblendable). To enable an emulsion the addition of emulsifiers is necessary. Emulsifiers are generally surfactants, co-surfactants or co-solvents, such as cetearyl alcohol, polysorbate 20 and ceteareth 20 or polyethylene glycol, and others as known by skilled artisans.

The topical formulation can be applied to skin or mucosa. Mucosal tissues with which the topical formulation can be used include for example nasal (including olfactory), vaginal, anorectal, penile, oral, buccal and bronchial tissue.

When lipid vesicles or lipid particles are present, the skin barrier repair formulation may have added PEGylated lipids or other lipids conjugated with hydrophilic polymer in amounts that stabilize these aggregate forms.

Information on Humectants, Emollients, Osmolytes, Moisturizers and Occlusive Agents There has always been some confusion between what a moisturizer is and what a humectant is, especially where the consumer is concerned. To put it simply, a moisturizer is any substance or mixtures of chemical agents specially designed to make the external layers of the skin or epidermis softer and more pliable, by increasing their hydration or water content. In contrast to this, a humectant is any substance that is hygroscopic and can absorb water from the air. Humectants are usually molecules with one or more hydrophilic groups attached to them. These hydrophilic groups can either be amines (—NH3) such as urea or amino acids, carboxyl groups (—COOH) such as fatty acids or alpha hydroxy acids, or hydroxyl groups (—OH) such as glycerin, sorbitol and butylene glycol or other glycols. The key functionality of a humectant is to form hydrogen bonds with molecules of water. Although very similar in function, moisturizers can be naturally occurring skin lipids and sterols, as well as naturally occurring or synthetic emollients, fats, or lubricating oils. Some substances fall in both classes.

Osmolytes. Osmolytes are compounds affecting osmosis. They are soluble in the fluids within a cell, or in the surrounding extracellular environment e.g. as plasma osmolytes. They play a role in maintaining cell volume and fluid balance. For example, when a cell swells due to external osmotic pressure, membrane channels open and allow efflux of osmolytes which carry water with them, restoring normal cell volume. Osmolytes also contribute to protein folding. Natural osmolytes that can act as osmoprotectants include trimethylamine N-oxide (TMAO), dimethylsulfoniopropionate, trimethylglycine, sarcosine, betaine, glycerophosphorylcholine, myo-inositol, taurine, glycine, alanine and others.

Humectants. Humectants include ingredients such as glycerin, urea, pyrrolidone carboxylic acid (PCA), hyaluronic acid, or the like. These materials function by attracting water outward to the stratum corneum (SC) from the dermis below and binding that water in the SC. Glycerin, for instance, frequently is used due to its low cost and high efficacy. However, the tacky feeling imparted to skin by high levels of humectants is one of the drawbacks to formulating with them. Thus, when optimizing skin formulations, cosmetic chemists often are challenged to reduce these negative properties. Certain amino acids such as alanine are humectants. In certain embodiments, hyaluronic acid or a salt thereof is included, such as for example in an amount from about 0.1% by weight to about 5%.

Occlusive Agents. Occlusive agents increase moisture levels in skin by providing a physical barrier to epidermal water loss. Ingredients with occlusive properties include petrolatum, waxes, oils and silicones. Some occlusive agents like petrolatum can leave a heavy feeling on skin; thus they often are combined with other ingredients like emollients to improve consumer appeal.

Emollients. Emollients provide some occlusivity and improve the appearance of the skin by smoothing flaky skin cells. Many different types of emollient esters and oils are available to formulators. Emollients generally are grouped by their ability to spread on the skin. By combining emollients with the different spread rates, formulators can tailor the skin feel of a moisturizer. One can test for these differences by using different emollients in a standard base lotion or other composition. Additionally, emollient lipids similar to those naturally found in the skin may also increase the rate of barrier repair, for example as ceramides, steroids, sterol esters or fatty acids. Emollients are often polymeric, and include silicone compounds, but further include petrolatum.

Combining Forces. Each of these ingredient types has a different mechanism of action and most cosmetic moisturizers will use a combination of them.

Vesicles

Embodiments of the invention can include one or both of two types of lipid aggregates, lipid particles and lipid vesicles, defined below. These are typically produced separately, and can be combined for use. The fraction used to create the vesicles can be termed the "ultra-fine fraction."

Using lipid compositions such as are described herein, bilayer-enclosed vesicles can be made typically with methods that direct sufficient oscillatory energy or other means (e.g. mechanical or thermal) per unit volume—at once or by serially applying such energy to different sub-volumes. Sonicating devices, for example, can be used. Or, appropriate high pressure homogenizers can be used, such as of a Rannie homogenizer from Invensys APV (Fluid Handling & Homogenisers, Lake Mills, Wis.). The pressure of the homogenizer can be set, for example, from about 10,000 to 40,000 psi, such as 21,756 psi (1500 bar). An example of a sonicator is Soniprep 150, manufactured by Sanyo Gallencamp Plc. Ultrasound radiation is transmitted by high frequency vibrations via a titanium alloy probe from a transducer that converts electrical energy to mechanical energy. The diameter of the probe tip can vary. An example of a diameter of a probe tip is about 9.5 mm. The amplitude at which the sonication can be performed can vary. An example of an amplitude is 10 microns for 30 minutes.

The vesicle formation is typically conducted at a relatively elevated temperature, such as a temperature of 45° C. or more, or 50° C. or more, or 55° C. or more, or 60° C. or more, or 65° C. or more. The temperature can, for example, be 75° C. or less, or 70° C. or less, or 65° C. or less. The bioactive agent(s) may affect the choice of temperature, with the temperature moderated for more labile bioactive agents. The pH obtained from the vesicle formation can be selected in view of the properties of the bioactive agent.

Without being bound to theory, it is believed that the use of smaller vesicles with associated bioactive agent can provide faster initial uptake of the bioactive agent. Thus, depending on the pharmacokinetic profile desired, the amount and size of the vesicles can be varied. Typically, to obtain smaller vesicles, more energy has to be applied to the production process. For example, using the Rannie homogenizer, it may be appropriate to pass the production suspension two or more times through a homogenization cycle. Delays and cooling between the applications of energy can minimize excess heating.

In certain embodiments, the average vesicle size can be, for example, 500 nm or less, or 450 nm less, or 400 nm less, or 350 nm less, or 300 nm less, or 250 nm less, or 200 nm less, or 150 nm less, or 100 nm less. And/or, the average vesicle size can be, for example, 20 nm or more, or 30 nm more, or 40 nm more, or 45 nm more, or 50 nm more, or 75 nm more, or 100 nm more, or 150 nm more, or 200 nm more. Size determination can be by light scattering, using a Malvern Autosizer (Malvern Instruments Ltd., Malvern, Worcestershire, UK), or a device calibrated to give comparable results.

Electron-microscopic analysis shows that the predominate morphology of lipid aggregates is unilamellar vesicles.

The vesicles can comprise fatty acid (FA), bilayer-stabilizing steroid (CH), and complex lipid (CL).

Lipid Particles

The fraction used to create the lipid particles can be termed the "disperse fraction."

The lipid particles can be made by passing aqueous suspensions of the lipid components through dispersing equipment, such as the Dispermix device from Ystral GmbH (Ballrechten-Dottingen, Germany). These particles typically have a wide size distribution, which is typically of sizes larger than found in the ultra-fine fraction, such as from 1000 nm (1 micron). In some embodiments, the upper sizes may be as high as 20 or 30 microns. Average size can be determined by measuring an appropriate sampling by microscope.

Particle formation is typically conducted at a relatively elevated temperature, such as a temperature of 45° C. or more, or 50° C. or more, or 55° C. or more, or 60° C. or more, or 65° C. or more. The temperature can, for example, be 75° C. or less, or 70° C. or less, or 65° C. or less. The bioactive agent(s) may affect the choice of temperature, with the temperature moderated for more labile bioactive agents. The pH obtained from the particle formation can be selected in view of the properties of the bioactive agent.

Without being bound by theory, it is believed that the particles are predominantly surrounded by a lipid monolayer. Lipid components can be selected such that both the ultra-fine fraction and the disperse fraction can be formed from substantially the same lipids.

Mixing Fractions

The disperse fraction and the ultra-fine fraction can be mixed to form the delivery system. When conducting this mixing, care can be taken to avoid temperatures above a given boundary, such as 35° C.

The amount of bioactive agent in each of the lipid fractions, and the relative amount of the lipid components of the fractions can be varied as indicated by empirical studies of the resulting pharmacokinetic profile.

Surprisingly, compositions of the invention have been found to incorporate into mucosal tissue, in contrast to a number of topical lotions or creams, that cake when applied to such tissue. Without being bound by theory, it is believed that the above-described small sizes for vessels or lipid particles (in contrast to emulsions) is responsible for this useful effect. By incorporation it is meant that when a moisturizing useful amount is applied to mucosal tissue, any caking (agglomeration, undispersed product) disappears within about 5 seconds.

Mucosal Spraying

Any spray device, such as those used for Afrin nasal sprays, can be used to deliver bioactive agent to mucosal tissue or systemically (transmucosal delivery). As will be recognized by those of skill in the art, more than one source vessel can be used to hold the composition, or parts thereof, prior to spraying. Mixing formulations, such as formulations that are separately predominantly vesicles and that are predominantly lipid particles, can be incorporated into the plumbing in which streams from two source vessels are joined.

Conjugated Lipid

A conjugate of a lipid-phase anchoring hydrophobic moiety and a flexible, soluble polymer can be, for example, a conjugate of a type A lipid and a polymer such as polyethylene glycol. Other hydrophobic materials can be used to anchor the polymer to a lipid or bilayer phase, so long as the association is sufficiently stable. One exemplary conjugate is distearoyl-phosphatidylethanolamine-polyethylene glycol (DSPE-PEG). The conjugated polyethylene glycol can have an average molecular weight of, for example 2000. In certain embodiments, the average molecular weight of the flexible, soluble polymer is 500 or more, 750 or more, or 1000 or more. In certain embodiments, the average molecular weight of the polymer is 5000 or less, 4000 or less, or 3000 or less.

If present, the contribution of the lipid anchor portion of the conjugate to the overall aggregate-forming lipid is typically relatively low, such as 10 mole % or less. In certain embodiments using the conjugate, the contribution is 9 mole % or less, or 8 mole % or less, or 7 mole % or less, or 6 mole % or less, or 5.5 mole % or less, or 5 mole % or less. In certain embodiments using the conjugate, the contribution is 1 mole % or more, or, 2 mole % or more, or, 3 mole % or more, or, 4 mole % or more, or, 4.5 mole % or more, or, 5 mole % or more.

Other polymers besides polyethylene glycol can be used, provided sufficient biocompatibility, flexibility and water solubility. Without being bound to theory, it is believed that the polymer stabilizes the lipid aggregates by physically keeping them separate, thereby limiting fusions that change the properties of the lipid aggregates. Other flexible, soluble polymers can include polyvinylpyrrolidone (PVP), polyvinyl alcohol (PVA), monosial ganglioside, and the like.

Without being bound to theory, it is believed that the conjugate, while stabilizing the lipid aggregates in the composition before use, also help adhere lipid aggregates to the skin or mucosal membrane as the composition spreads along such skin or membrane. This latter function can be substituted, to some degree, with optional non-anchored hydrophilic polymer, such as PEG or PVP or PVA. This latter function can be applied in the absence of substantial amounts of vesicles and lipid particles.

Specific embodiments according to the methods of the present invention will now be described in the following examples. The examples are illustrative only, and are not intended to limit the remainder of the disclosure in any way.

Definitions

The following terms shall have, for the purposes of this application, the respective meanings set forth below.

Bioactive Agent

A bioactive agent is a substance such as a chemical that can act on a cell, virus, tissue, organ or organism, including but not limited to drugs (i.e., pharmaceuticals) to create a change in the functioning of the cell, virus, organ or organism to achieve a pharmaceutical or therapeutic effect. Where recited in a claim reciting the presence of (1) three or more of the following four components a through d, or (2) component c and one or more of components a, b or d, the bioactive agent is an agent separate from those components.

Cell-Surface Disruptor

A cell surface disruptor is (a) a detergent or (b) an organic solvent; wherein such detergent is (a) a micelle-forming detergent that is stronger than phospholipid, ceramide(s), sphingomyelin(s) or glucocerebroside(s) (in a form typically found in cell membrane) and (b) not a fatty acid or salt thereof that is C8 or higher. A "modified cell-surface disruptor" is not a fatty acid or salt thereof that is C10 or higher.

Essentially Lacking a Cell-Surface Disruptor

A composition (or formulation) is essentially lacking cell-surface disruptors if the amount present is zero or less than the amount that can cause irritation by cell-surface disruption. For example, a cell-surface disruptor might be present due to its use in facilitating the formulation of the composition (such as a carrier for a component that will be substantially diluted), but the amount in the final composition will be of no consequence as a cell-surface disruptor.

Flexible, Soluble Polymer

A flexible, soluble polymer is a polymer effective to, when positioned on and linked to the outside of a bilayer-enclosed vesicle, to increase the stability of the vesicle.

Lipid Particle

Lipid particles are the result from melting the lipid fraction (described above) in conjunction with mild homogenization and letting it to cool. Lipid particles may thus be relatively heterogeneous, containing for example large or small particles, micro scale lumps, crystals, bilayer fragments and or multilamellar vesicles of different sizes and lamillarity, or the like. They are aggregates of lipid that contain a contiguous segment of lipid, or are substantially multilamellar (i.e., can by microscopic examination be estimated to have 80% of its lipid content weight in multilamellar structures).

Lipid-Phase Anchoring Hydrophobic Moiety

A lipid-phase anchoring hydrophobic moiety is used as a covalent conjugate with a flexible, soluble polymer. The lipid-phase anchoring hydrophobic moiety associates, for example, with the bilayer of a vesicle with sufficient stability to keep conjugated polymer predominantly anchored to lipid and positioned to increase the stability of the vesicles.

Lipid Vesicles

Lipid vesicles are lipid aggregates that are unilamellar vesicles. These can include minor amounts (<about 20% by lipid content weight) of unilamellar vesicles that incorporate 1-8 other unilamellar vesicles (separately within, or serially inclusive in nesting doll fashion).

Treatment

"Treating" a disease, disorder or condition includes ameliorating the symptoms of the disease, disorder or condition, or delaying or ameliorating the progression or initiation of disease, disorder or condition, including symptoms or complications thereof. Given appropriate bioactive agents, any animal can be treated, including mammals such as humans.

Additional terms are defined in context in the discussion above.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

Example 1—Transepidermal Water Loss Measurement

In certain measurements, skin, such as human or pig skin, is disrupted by applying 1% or 10% (w/w) solution of sodium dodecyl sulfate (SDS, also referred to as sodium lauryl sulfate or SLS), or an amount therebetween.

Protocol for Measuring Transepidermal Water Loss (TEWL) after Challenge with Drying Agent or Irritant Surfactant Such as SDS:

For humans, the subject will clean the left forearm prior to visit without scrubbing. The patient will acclimate to the office environment for 30 min prior to baseline measurement and application of a skin drying agent and prospective treatment compositions (such as creams). The volar surface of the left forearm will be marked using a sharpie with 4 circles about the size of a quarter. The TEWL meter will measure all areas (circle 1, 2, 3, 4 and 5) as a baseline after the 30 min acclimation period. The forearm circled areas 2, 3, and 4 will be treated with a drying agent such as 1% SLS on an applicator tip. The closest circle to the hand (circle 1) will serve as an untreated control. Circle 2 will receive SLS only. After 30 min of treatment with SLS circles 3, 4 and 5 will receive the positive control, test composition and test composition minus taurine and retinoid, respectively. Circle 3 will receive a positive control product such as cetaphil restoraderm. The forth circle (circle 4) will receive the test composition. Circle 5 (if used) will receive the test composition formulated without retinoid and without taurine ($T_{minus}$ Composition). The compositions (circles 3-5) will be applied and rubbed into the marked area until absorbed onto the skin (about a minute). The moisture meter will measure all circles at 30 min 1, 2, and 3 hrs post treatment. In embodiments, measurements are continued, such as for intervals including 48 hrs.

Results are measured for skin and mucosa.

Protocol for Measuring TEWL:

For humans, the subject will clean the right arm prior to visit without scrubbing. The patient will acclimate to the office environment for 30 min prior to baseline measurement and application of prospective treatment compositions (such as creams). The volar surface of the right forearm will be marked using a sharpie with 3 circles about the size of a quarter. The TEWL meter will measure all areas (circles 1, 2, 3 and 4) as a baseline after the 30 min acclimation period. The closest circle to the hand (circle 1) will serve as an untreated control. The middle circle (circle 2) will receive a positive control product such as cetaphil restoraderm. The third circle (circle 3) will receive the test composition. The fourth circle (if used) will receive the test composition formulated without retinoid and without taurine ($T_{minus}$ Composition). The creams (circle 2-4) will be applied and rubbed into the marked area until absorbed onto the skin (about a minute). The TWEL meter will measure all circles at 30 min 1, 2, 3, and 24 hrs post treatment. In embodiments, measurements are continued, such as for intervals including 48 hrs.

Results are measured for skin and mucosa.

Example 2—Skin Moisture Measurement

For human subjects, the subject will clean the right arm prior to visit without scrubbing. The subject will acclimate to the office environment for 30 prior to baseline measurement and application of compositions (such as creams). The volar surface of the right arm will be marked using a sharpie with 3 circles about the size of a quarter. The moisture meter (e.g., corneometer measuring conductance or resistance) will measure all areas (circle 1, 2, 3 and 4) as a baseline after the 30 min acclimation period. (Despite the skin-derived nomenclature for the device, the moisture meter will function with mucosa.) The closest circle to the hand (circle 1) will serve as an untreated control. The middle circle (circle 2) will receive the positive control product such as cetaphil restoraderm. The third circle (circle 3) will receive the test cream. The fourth circle (if used) will receive the test composition formulated without retinoid and without taurine ($T_{minus}$ Composition). The compositions (circles 2-4) will be applied and rubbed into the marked area until absorbed onto the skin (about a minute). The moisture meter will measure all circles at 30 min 1, 2, 3, and 24 hrs post treatment. In embodiments, measurements are continued, such as for intervals including 48 hrs.

Results are measured for skin and mucosa.

Example 3—Moisture Measurements with Corneometer

The treatment method was applied after challenge with drying agent or irritant surfactant. In this method, the higher the conductance, the better the moisturizing efficiency. The treatments were:

| A | Control: No Treatment |
| B | Composition with components a, b, c and d. |
| C | Composition with components a and b. |

Study Method:

The forearm skin was washed for one minute twice a day for two days using 10% SLS (SDS). On day 3, 0.1 ML of products B and C were applied to a 2×2 inch area of the forearm and while area A was untreated to serve as a negative control.

The conductance measurements (arbitrary units) were:

| 5 min | | |
| --- | --- | --- |
| A = 28.6 | B = 39.5 | C = 40.9 |
| 10 min | | |
| A = 22.7 | B = 26.1 | C = 26.6 |
| 15 min | | |
| A = 17.6 | B = 24 | C = 21.9 |
| 30 min | | |
| A = 17.8 | B = 24.7 | C = 19.3 |
| 45 min | | |
| A = 15.3 | B = 26.6 | C = 23 |
| 60 min | | |
| A = 16.7 | B = 25.4 | C = 21 |

Both products (B and C) were significant better moisturizers than control (A no treatment). Product B was significantly better as early as 15 minutes post treatment compared to product C and maintained higher hydration throughout the 60 minutes evaluation period. These data demonstrate that adding Taurine and a Retinoid significantly increases skin conductance and hydration of the skin.

Example 4

An exemplary formulation of the invention is as follows (by weight):

| Component | Amount (%) |
| --- | --- |
| Phospholipon 90H | 1-6 |
| (Phosphatidylcholine, hydrogenated) | |
| Sodium PCA | 0.1-6 |
| Palmitic acid | 0.5-4 |
| Cholesterol | 0.5-4 |
| Taurine | 0.1-5 |
| Retinol | 0.1-10 |
| Ceramide III | 0.05-0.5 |
| UCA | 0.05-3 |
| Hyaluronic acid (or, e.g., a salt thereof) | 0-5 |
| $K_2HPO_4$ | 0.43 |
| $KH_2PO_4$ | 0.34 |
| Benzalkonium chloride | 0.09 |
| Xanthan gum | 0.3 |
| 5M NaOH | as needed |
| Tyrosine | 0.1-2 |
| Glycerine | 0-5 |
| Water | To 100% |

An appropriate thickening agent such as hydroxyethyl cellulose can be added for the purposes of adjusting viscosity so that dosing forms ranging including but not limited liquids, lotions, gels, creams and ointments.

If the formulation is to be a foam, an appropriate foaming agent, such as laureth-4, is added.

Example 5

For Examples 5 to 7, a formulation consistent with the following was used:

| Component | Amount (%) |
|---|---|
| Phospholipon 90H (Phosphatidylcholine, hydrogenated) | 1-6 |
| Sodium PCA | 0.1-6 |
| Palmitic acid | 0.5-4 |
| Cholesterol | 0.5-4 |
| Taurine | 0.1-5 |
| Retinol | 0.1-10 |
| Ceramide III | 0.05-0.5 |
| UCA | 0.05-3 |
| Hyaluronic acid (or, e.g., a salt thereof) | 0-5 |
| $K_2HPO_4$ | as appropriate |
| $KH_2PO_4$ | as appropriate |
| Preservative | as appropriate |
| Xanthan gum | 0.1-0.8 |
| 5M NaOH | as needed |
| Tyrosine | 0.1-2 |
| Glycerine | 0-5 |
| Water | To 100% |

Figure 3:
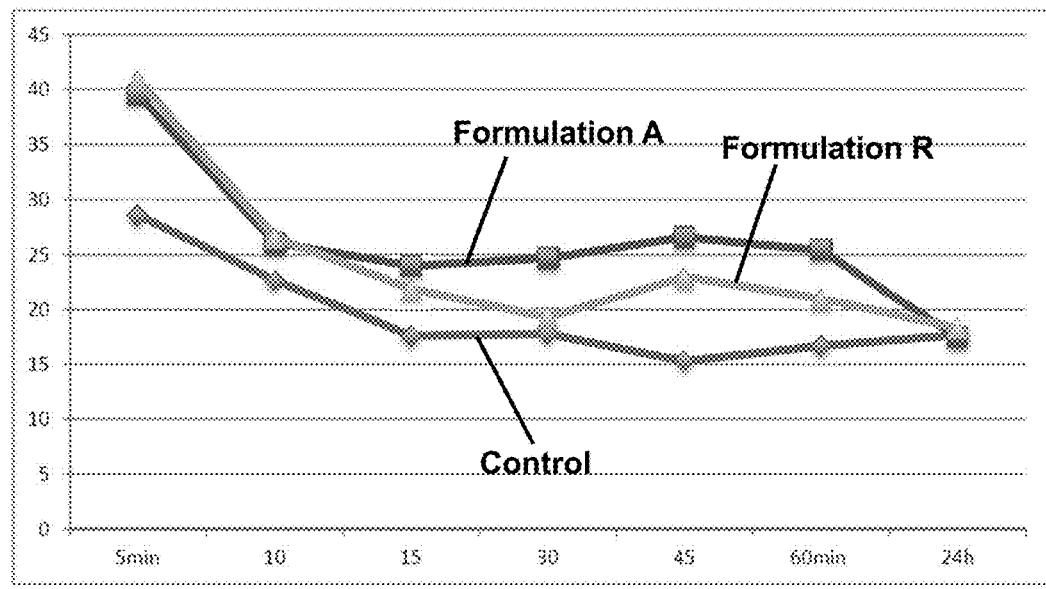
FIG. 3 is a comparison over time of the moisture level of skin that is untreated, treated with a formulation of the invention, and treated with a comparative formulation having only component (a) of the components recited above.

The above formulation ("Formula A") was compared to no treatment control, and to the above formulation lacking components (b) {PCA and UCA}, (c) {retinol} and (d) {taurine} ("Formula R") for moisturizing volunteer skin. For two volunteers, the forearm skin was washed for one minute twice a day for two days using 10% SLS (SDS). On day 3, 0.1 ML of Formulas A and R were applied to a 2×2 inch area of the forearm and while an area on the other arm was untreated to serve as a negative control. The average moisture results (arbitrary units) are tabulated below and shown in FIG. 3.

| Skin Moisture | | | | | | | |
|---|---|---|---|---|---|---|---|
| | 5 min | 10 | 15 | 30 | 45 | 60 min | 24 h |
| Control | 28.6 | 22.7 | 17.6 | 17.8 | 15.3 | 16.7 | 17.7 |
| Formula A | 39.5 | 26.1 | 24 | 24.7 | 26.6 | 25.4 | 17.5 |
| Formula R | 40.9 | 26.6 | 21.9 | 19.3 | 23 | 21 | 18.3 |

The measurements were made with a Delfin MoistureMeter SC (Delfin Technologies Ltd., Kuopio, Finland) moisture meter.

The control shows that under the ambient conditions of the test, the skin was losing moisture. However, consistently better skin moisture was found during the 15 min to 60 min period for the skin treated with Formulation R (prior art), and still better skin moisture was found during the 5 min to 60 min period for the skin treated with Formulation A.

Example 6

For this test of water evaporation from the skin, Formulation A1 was as above for Formulation A (lacking hyaluronic acid), and Formulation A2 was the same, but adding hyaluronic acid. The comparative was Formulation R. A no treatment control was used to normalize the data. Under non-stressed conditions, healthier skin evaporates less water. A VaporiMeter (Delfin Technologies was used for TEWL measurements. Measurements were preformed in triplicate. Standard deviation was less than 10% of the mean value.

Figure 4:
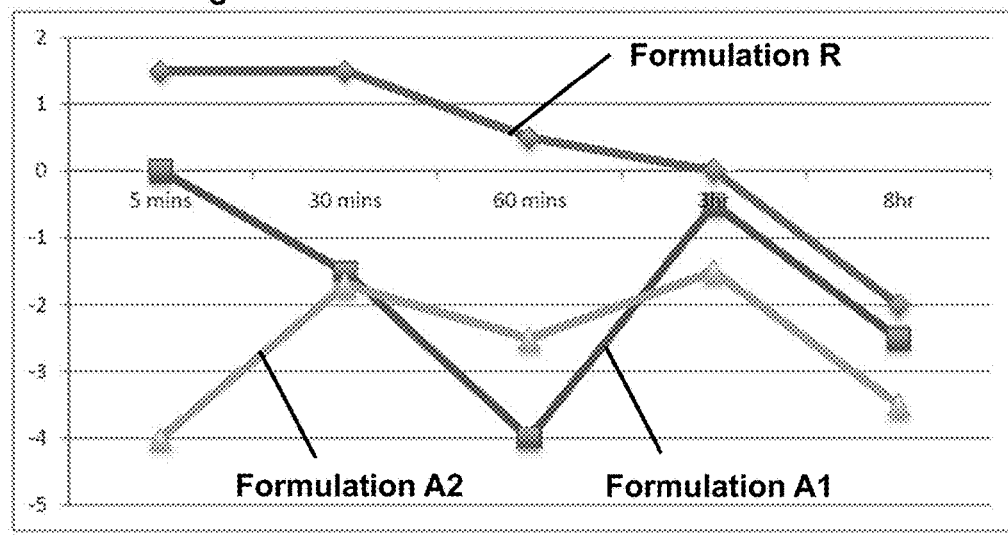
FIG. 4 is a comparison, versus control, of two formulations of the invention, and the component (a) formulation, with respect to water evaporation from the skin.

The results are shown in FIG. 4, and tabulated below:

| Transepidermal Water Loss (Normalized Against Control) | | | | | |
|---|---|---|---|---|---|
| | 5 mins | 30 mins | 60 mins | 3 hr | 8 hr |
| Formulation R | 1.5 | 1.5 | 0.5 | 0 | -2 |
| Formulation A1 | 0 | -1.5 | -4 | -0.5 | -2.5 |
| Formulation A2 | -4 | -1.7 | -2.5 | -1.5 | -3.5 |

The results show that Formulations A1 and A2 improve skin function by this measure.

Example 7

In this test, Formulation A2 was compared to no treatment control, and two leading commercial products. The forearms were washed for one minute twice per day for two days with 10% SLS. On the third day, 4 areas (approximately) 2 inch by 2 inch) were used on both forearms. Formulation A2, Cepaphil cream, Olay Regenerist cream or control (no cream) was applied to cover each area. One square was left without application of cream to serve as an untreated control. At various times post application transepidermal water loss was measured using a Delphin VapoMeter TEWL meter. Measurements were preformed in triplicate. Standard deviation was less than 10% of the mean value.

Figure 5:
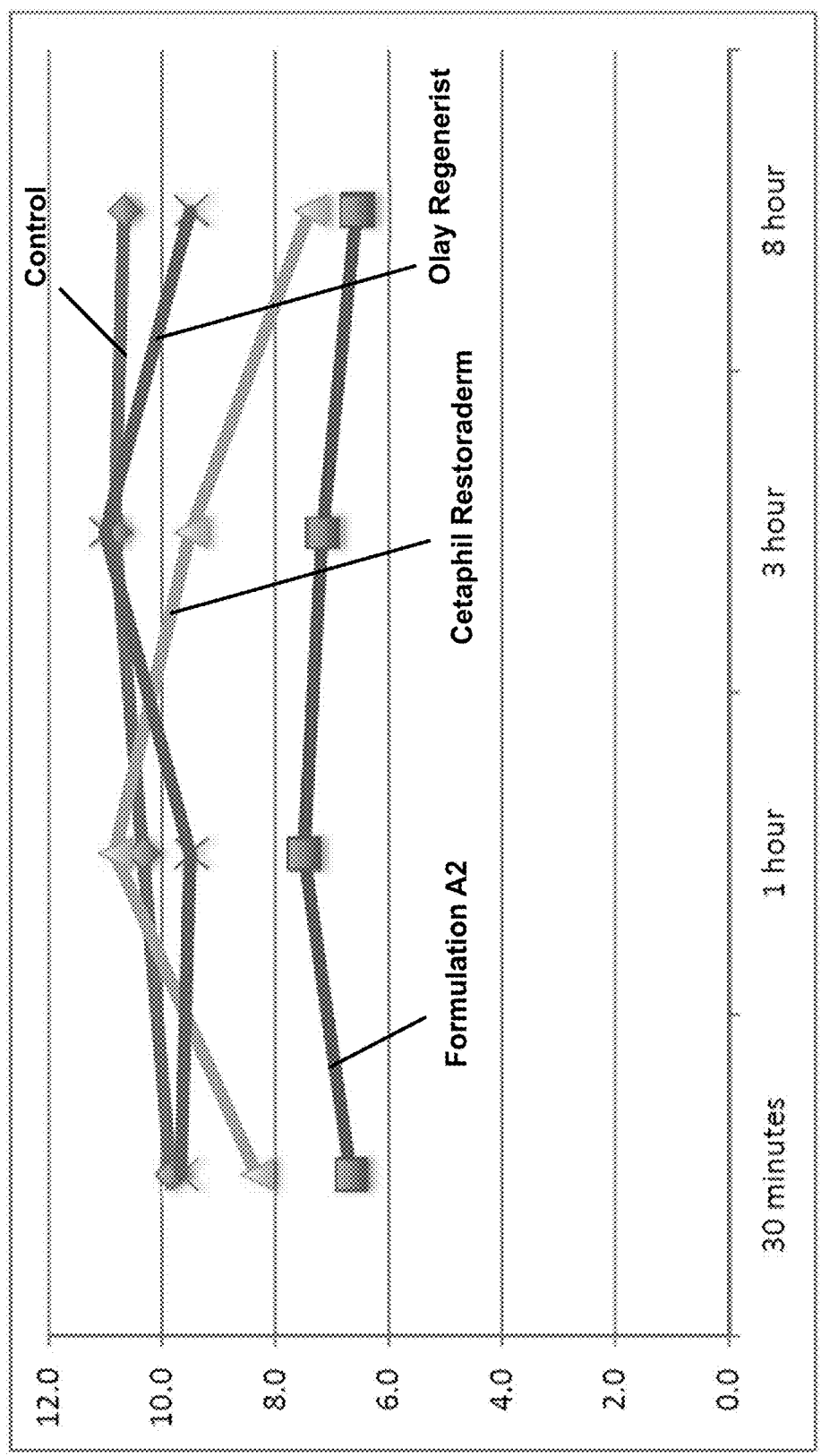
FIG. 5 is a comparison of trans epidermal water loss for a formulation of the invention versus two leading commercial products.

The average results (units=$g/m^2/hr$) are shown in FIG. 5, and tabulated below:

| Transepidermal Water Loss | | | | |
|---|---|---|---|---|
| | 30 minutes | 1 hour | 3 hour | 8 hour |
| Control | 9.8 | 10.3 | 10.8 | 10.7 |
| Formulation A2 | 6.7 | 7.5 | 7.2 | 6.6 |
| Cetaphil Restoraderm | 8.3 | 10.8 | 9.5 | 7.4 |
| Olay Regenerist | 9.7 | 9.5 | 11.0 | 9.5 |

As can be seen, Formulation A2 is markedly superior to the commercial products. After a considerable lag period, one competing product begins to catch up.

The invention can be further described with respect to the following numbered embodiments:

Embodiment 1

A topical formulation comprising (1) three or more of the following four components a through d, or (2) component c and one or more of components a, b or d: (a) a skin barrier repair formulation comprising lipids that are fatty acid (FA), bilayer-stabilizing steroid (CH), and complex lipid (CL), wherein the skin barrier repair formulation is present in an amount that enhances skin barrier repair, wherein the weight ratio of CL to CH is from about 1.5:1 to about 8:1, and the weight ration of CL to FA is from about 4:1 to about 1:1, the lipids present in an amount from about 3% wt. to about 10% wt.; (b) a natural moisturizer formulation, wherein the natural moisturizers are selected from the group consisting of urea, urocanic acid (UCA), pyrrolidone-5-carboxylic acid (PCA), lactic acid and free amino acid, the natural moisturizer formulation present in a skin moisturizing amount; (c) one or more retinoids in an amount from about 0.01% wt. to about 10% wt.; or (d) taurine in an amount from about 0.1% wt. to about 5% wt, wherein if the formulation comprises components a and c, then it further comprises one or more of b and d.

Embodiment 2

The formulation of Embodiment 1, wherein component c is present.

Embodiment 3

The formulation of Embodiment 2, wherein component a is present.

Embodiment 4

The formulation of Embodiment 2, wherein component b is present.

Embodiment 5

The formulation of Embodiment 2, wherein component d is present.

Embodiment 6

The formulation of Embodiment 1, wherein components a, b and c are present.

Embodiment 7

The formulation of Embodiment 1, wherein components a, c and d are present.

Embodiment 8

The formulation of Embodiment 1, wherein components b, c and d are present.

Embodiment 9

The formulation of Embodiment 1, wherein components a, b, c and d are present.

Embodiment 10

The formulation of one of Embodiments 1-9, wherein component a is present and comprises vesicles of average size from about 20 to about 500 nm.

Embodiment 11

The formulation of one of Embodiments 1-9, wherein component a is present and comprises lipid particles of average size from about 1 to about 30 microns.

Embodiment 12

The formulation of one of Embodiments 1-9, wherein component a is present and comprises (i) vesicles of average size from about 20 to about 500 nm and (ii) lipid particles of average size from about 1 to about 30 microns.

Embodiment 13

The formulation of one of Embodiments 10 to 12, wherein the formulation if tested by application on mucosal tissue incorporates therein (into the tissue).

Embodiment 14

The formulation of one of Embodiments 1-13, further comprising a bioactive agent.

Embodiment 15

A method of delivering a bioactive agent to skin or mucosa, or systemically, comprising applying the formulation of Embodiment 14 to the skin or mucosa.

Embodiment 16

The method of Embodiment 15, wherein the formulation is applied to the skin.

Embodiment 17

The method of Embodiment 15, wherein the formulation is applied to vaginal mucosa.

Embodiment 18

The method of Embodiment 15, wherein the formulation is applied to intranasal mucosa.

Embodiment 19

A method of moisturizing skin comprising applying to the skin a formulation of one of Embodiments 1-13.

Embodiment 20

A method of moisturizing mucosa comprising applying to the mucosa a formulation of one of Embodiments 1-13.

This invention described herein is of a topical formulation methods of delivering a bioactive agent to skin or mucosa, or systemically using the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A water-based topical formulation comprising following components a, b, c and d:
   (a) a skin barrier repair formulation comprising lipids that are free fatty acid (FFA), bilayer-stabilizing steroid (CH), and complex lipid (CL), wherein the skin barrier repair formulation is present in an amount that enhances skin barrier repair, wherein the weight ratio of CL to CH is from about 1.5:1 to about 8:1, and the weight ratio of CL to FA is from about 4:1 to about 1:1, lipids present in an amount from about 3% wt. to about 10% wt. of the topical formulation, wherein complex lipids are phospholipid or ceramide or mixtures thereof in a form that can be incorporated in lipid bilayers;

(b) a formulation of natural moisturizer factor(s), comprising natural moisturizer factors selected from the group consisting of urocanic acid (UCA), pyrrolidone-5-carboxylic acid (PCA) and combinations thereof, the natural moisturizer factor formulation present in a skin moisturizing amount of 0.1% wt. to about 10% wt. of the topical formulation, the natural moisturizers contributing to the percent amount being amino acids, UCA and PCA, wherein UCA if present is in an amount from 0.05% to 3% wt. of the topical formulation, wherein PCA if present is in an amount from 0.1% to 3% wt. of the topical formulation;

(c) one or more retinoids in an amount from about 0.1% wt. to about 5% wt., wherein the amount is effective to activate or upregulate TauT; and (d) taurine in an amount from about 0.1% wt. to about 5% wt, wherein the formulation at a dosage is effective to reduce, relative to a no-treatment control, TEWL on human skin 60 minutes or less after challenge with sodium dodecyl sulfate at 10 wt. %, wherein all component a compounds and all emollients or moisturizer agents in the formulation consist essentially of compounds found in skin, and wherein the topical formulation at the dosage is more effective in said 60 minute TEWL challenge than a comparable formulation having component a, but lacking components b, c and d.

2. The formulation of claim 1, wherein component a comprises vesicles of average size from about 20 to about 500 nm.

3. The formulation of claim 1, wherein component a comprises lipid particles of average size from about 1 to about 30 microns.

4. The formulation of claim 1, wherein component a comprises (i) vesicles of average size from about 20 to about 500 nm and (ii) lipid particles of average size from about 1 to about 30 microns.

5. The formulation of claim 2, wherein the formulation if tested by application on mucosal tissue incorporates therein.

6. The formulation of claim 1, further comprising a bioactive agent.

7. A method of delivering a bioactive agent to skin or mucosa, or systemically, comprising applying the formulation of claim 6 to the skin or mucosa.

8. The method of claim 7, wherein the formulation is applied to the skin.

9. The method of claim 7, wherein the formulation is applied to vaginal mucosa.

10. The method of claim 7, wherein the formulation is applied to intranasal mucosa.

11. A method of moisturizing skin comprising applying to the skin a formulation of claim 1.

12. A method of moisturizing mucosa comprising applying to the mucosa a formulation of 1.

13. The formulation of claim 1, wherein said comparable formulation having component a and any other occlusive compounds but lacking components b, c and d is approximately as effective in said 60 minute TEWL challenge as the no treatment control, or less effective.

14. A water-based topical formulation comprising following components a, b, c and d:

(a) a skin barrier repair formulation consisting essentially of lipids that are free fatty acid (FFA), bilayer-stabilizing steroid (CH), and complex lipid (CL), wherein the skin barrier repair formulation is present in an amount that enhances skin barrier repair, wherein the weight ratio of CL to CH is from about 1.5:1 to about 8:1, and the weight ratio of CL to FA is from about 4:1 to about 1:1, lipids present in an amount from about 3% wt. to about 10% wt. of the topical formulation, wherein complex lipids are phospholipid or ceramide or mixtures thereof in a form that can be incorporated in lipid bilayers;

(b) a formulation of natural moisturizer factor(s), comprising natural moisturizer factors selected from the group consisting of urocanic acid (UCA), pyrrolidone-5-carboxylic acid (PCA) and combinations thereof, the natural moisturizer factor formulation present in a skin moisturizing amount of 0.1% wt. to about 10% wt. of the topical formulation, the natural moisturizers contributing to the percent amount being amino acids, UCA and PCA, wherein UCA if present is in an amount from 0.05% to 3% wt. of the topical formulation, wherein PCA if present is in an amount from 0.1% to 3% wt. of the topical formulation;

(c) one or more retinoids in an amount from about 0.1% wt. to about 5% wt., wherein the amount is effective to activate or upregulate TauT; and (d) taurine in an amount from about 0.1% wt. to about 5% wt, wherein the formulation at a dosage is effective to reduce, relative to a no-treatment control, TEWL on human skin 60 minutes or less after challenge with sodium dodecyl sulfate at 10 wt. %, wherein all component a compounds and all emollients or moisturizer agents in the formulation consist essentially of compounds found in skin, and wherein the topical formulation at the dosage is more effective in said 60 minute TEWL challenge than a comparable formulation having component a, but lacking components b, c and d.

* * * * *